United States Patent
Blohm et al.

(10) Patent No.: US 9,936,972 B2
(45) Date of Patent: Apr. 10, 2018

(54) METHOD OF AUTOMATICALLY MONITORING THE PENETRATION BEHAVIOR OF A TROCAR HELD BY A ROBOTIC ARM AND MONITORING SYSTEM

(71) Applicants: Lutz Blohm, Möhrendorf (DE); Michael Martens, Weisendorf (DE); Philip Mewes, Nürnberg (DE)

(72) Inventors: Lutz Blohm, Möhrendorf (DE); Michael Martens, Weisendorf (DE); Philip Mewes, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 342 days.

(21) Appl. No.: 14/927,840

(22) Filed: Oct. 30, 2015

(65) Prior Publication Data
US 2016/0128781 A1 May 12, 2016

(30) Foreign Application Priority Data
Oct. 31, 2014 (DE) ........................ 10 2014 222 293

(51) Int. Cl.
*A61B 17/34* (2006.01)
*A61B 34/30* (2016.01)
(Continued)

(52) U.S. Cl.
CPC ...... *A61B 17/3403* (2013.01); *A61B 17/3476* (2013.01); *A61B 34/30* (2016.02);
(Continued)

(58) Field of Classification Search
CPC . A61B 17/34; A61B 17/3403; A61B 17/3476; A61B 2017/3405;
(Continued)

(56) References Cited

U.S. PATENT DOCUMENTS 5,086,401 A * 2/1992 Glassman ............... A61B 34/20
606/53
5,299,288 A * 3/1994 Glassman ............... A61B 34/20
606/130
(Continued)

FOREIGN PATENT DOCUMENTS

CN 1179224 A 4/1998
CN 101076284 A 11/2007
(Continued)

OTHER PUBLICATIONS

Chinese Office Action for related Chinese Application No. 201510731714.4 dated Aug. 22, 2017.
(Continued)

*Primary Examiner* — Ryan J Severson
(74) *Attorney, Agent, or Firm* — Lempia Summerfield Katz LLC

(57) ABSTRACT

A method for automatically monitoring the penetration behavior of a trocar held by a robotic arm and monitoring system is provided. The method and system automatically monitors the penetration behavior of a trocar held by a robotic arm and/or an instrument guided through the trocar into a body cavity through an incision in the surface of the body of a patient during a surgical procedure. At least one measured value is recorded, by which a change in a force effect on the surface of the body of the patient may be determined, and automatic evaluation of the measured value with regard to a reference measured value is conducted. Comparison of the change in the measured value or the change in the force effect with a threshold value is made, and an indication in the event of the threshold value being exceeded is outputted.

20 Claims, 2 Drawing Sheets

(51) Int. Cl.
*A61B 17/00* (2006.01)
*A61B 90/00* (2016.01)
(52) U.S. Cl.
CPC .............. *A61B 2017/00119* (2013.01); *A61B 2017/3405* (2013.01); *A61B 2017/3409* (2013.01); *A61B 2090/064* (2016.02); *A61B 2090/066* (2016.02); *A61B 2090/3937* (2016.02)
(58) Field of Classification Search
CPC .... A61B 2017/3407; A61B 2017/3409; A61B 2034/301; A61B 2034/302; A61B 2090/062; A61B 2090/064; A61B 2090/065; A61B 2090/066; A61B 34/30; A61B 34/32; A61B 34/35; A61B 34/70; A61B 34/77
See application file for complete search history.

(56) References Cited

U.S. PATENT DOCUMENTS

| | | | | |
|---|---|---|---|---|
| 5,408,409 A * | 4/1995 | Glassman | | A61F 2/46 128/920 |
| 6,522,906 B1 * | 2/2003 | Salisbury, Jr. | | A61B 1/313 600/102 |
| 7,831,292 B2 * | 11/2010 | Quaid | | A61B 34/20 345/156 |
| 8,010,180 B2 * | 8/2011 | Quaid | | A61N 1/372 600/424 |
| 8,108,072 B2 * | 1/2012 | Zhao | | G06K 9/3216 382/153 |
| 8,374,723 B2 * | 2/2013 | Zhao | | B25J 9/1689 318/568.11 |
| 2003/0040758 A1 * | 2/2003 | Wang | | A61B 34/70 606/130 |
| 2004/0106916 A1 * | 6/2004 | Quaid | | A61B 34/71 606/1 |
| 2006/0142657 A1 * | 6/2006 | Quaid | | A61B 17/1764 600/424 |
| 2006/0258938 A1 * | 11/2006 | Hoffman | | A61B 1/00193 600/424 |
| 2007/0038080 A1 * | 2/2007 | Salisbury, Jr. | | A61B 1/313 600/427 |
| 2008/0004633 A1 | 1/2008 | Arata et al. | | |
| 2009/0088897 A1 * | 4/2009 | Zhao | | G06K 9/3216 700/250 |
| 2009/0275823 A1 | 11/2009 | Ayati et al. | | |
| 2010/0168763 A1 * | 7/2010 | Zhao | | A61B 34/30 606/130 |
| 2010/0168918 A1 | 7/2010 | Zhao et al. | | |
| 2015/0196340 A1 | 7/2015 | Combrowski | | |
| 2016/0128781 A1 * | 5/2016 | Blohm | | A61B 17/3403 606/130 |
| 2017/0151025 A1 * | 6/2017 | Mewes | | A61B 34/10 |

FOREIGN PATENT DOCUMENTS

| | | |
|---|---|---|
| CN | 101448468 A | 6/2009 |
| DE | 102012104973 A1 | 3/2013 |

OTHER PUBLICATIONS

German Office action for related German Application No. 10 2014 222 293.1, dated Aug. 5, 2015, with English Translation.
Krupa, Alexandre et al.: "Achieving high-precision laparoscopic manipulation through adaptive force control," in: Advanced Robotics, vol. 18 No. 9, pp. 905-926; VSP and Robotics Society of Japan 2004, 2004.

* cited by examiner

METHOD OF AUTOMATICALLY MONITORING THE PENETRATION BEHAVIOR OF A TROCAR HELD BY A ROBOTIC ARM AND MONITORING SYSTEM

CROSS-REFERENCE TO RELATED APPLICATION

This application claims priority under 35 U.S.C. § 119 to German Patent Application No. 102014222293.1, filed on Oct. 31, 2014, the entire content of which is incorporated herein by reference.

BACKGROUND

A method for automatically monitoring the penetration behavior of a trocar held by a robotic arm and monitoring system is provided.

Medical technology endoscopic robotic systems with robotic arms may be used to assist the physician or surgeon during a surgical procedure. The robotic system may serve as a guide, carrier, and instrument holder. The motorized drives of the robotic system allow movements and positionings with a high repetitive accuracy while significantly relieving the burden on the surgeon. Robotic systems with robotic arms that may be moved by an operator's touch are also known; accordingly, interactive operation without conventional operating elements and control sticks is possible.

However, in general, robotic systems have previously only been used successfully where all parameters of the surroundings are fixed, predictable, or may be measured using the senses. Flexible parameters, such as the surface of the body of a patient during a laparoscopic operation, e.g. due to the abdominal area filled with gas such as $CO_2$, may not be calculated by way of parameters. Knowledge of the position of the abdominal wall is very important since the pivot point for an inserted instrument results therefrom. An optimally positioned pivot point is important so as few translatory forces as possible act on the abdominal wall of the patient during rotational movements of the robotically held and moved instrument.

The entry into a body cavity, such as e.g. the abdominal area, of a patient may be enabled by what is known as a trocar. The trocar is thrust through an incision in the skin and, even during removal of the instruments, dispatches the gas that has filled the abdominal area. The trocar has flexible penetration depth and, depending on the situation, is forced through to different depths, e.g. into the abdominal area filled with gas. During a manually conducted procedure with an instrument, a surgeon constantly observes the deformation of the abdominal area in order to compensate gas that potentially needs to escape or released gas during the surgeon's movements. An incorrect application of force, and therewith possible complications, may be avoided by way of the perceived force application. Without knowledge of the pivot point, the surgeon manually moves or controls the instrument himself completely in all degrees of freedom. The surgeon constantly visually monitors the pressure in the abdominal area or responds to insufflator alarms. Alternatively, manual compensation by the surgeon is absent if the instrument is held or guided by suitable robotic systems.

BRIEF SUMMARY

The scope of the present invention is defined solely by the appended claims and is not affected to any degree by the statements within this summary. The present embodiments may obviate one or more of the drawbacks or limitations in the related art.

It is the object of the embodiments to provide a method simplifying use of endoscopic robotic systems; a further object of the embodiments is to provide a system suitable for carrying out the method.

The object is achieved by a method for automatically monitoring the penetration behavior of a trocar held by a robotic arm and/or an instrument guided by the trocar and by a monitoring system. Advantageous embodiments are also disclosed.

The method for automatically monitoring the penetration behavior of a trocar held by a robotic arm and/or an instrument guided through the trocar into a body cavity through an incision in the surface of the body of a patient during a surgical procedure includes the following acts: recording at least one measured value by which a change in a force effect on the surface of the body of the patient may be determined, automatic evaluation of the measured value with regard to a reference measured value, comparison of the change in the measured value or the change in the force effect with a threshold value, and outputting an indication in the event of the threshold value being exceeded. The reference measured value may have been recorded e.g. before or at the beginning of the surgical method or at least at one other time. The threshold value may be determined or fixed in advance. The indication may be output visually, acoustically, or haptically in the form of a signal or an alarm. Monitored changes associated with a force effect on the surface of the body of a patient may be caused by a change in air pressure in the patient, a deformation of organs (resection, change in position, etc.) or by external effects.

A surgical procedure may easily be automatically monitored by way of the embodiment. Monitoring has previously been carried out manually by a physician or other monitoring staff and is therefore susceptible to faults. In case of deviations in the penetration behavior, a countermeasure may now be taken quickly and effectively by way of the embodiment to avert injury to the patient and, by correcting the penetration behavior, to steer the procedure back onto the desired path. Undesirably changed, penetration behavior may lead to the procedure either injuring the patient or not leading to the desired result. If an undesirable change is detected quickly, and the person carrying out the procedure is made aware of the undesirable change, the course of the surgical procedure may also be accelerated and the situation that is stressful for the patient and staff may be curtailed.

A monitoring system for automatically monitoring the penetration behavior of a trocar held on a robotic arm and/or an instrument guided through the trocar into a body cavity through an incision in the surface of the body of a patient during a surgical procedure is provided via at least one measuring system for determining and recording a measured value from which a change in a force effect on the surface of the body of the patient may be determined. An evaluation device for evaluating the measured value and an output device for outputting an indication may also be provided.

According to an embodiment, the measured value is evaluated with regard to the change in the force effect. In addition to the evaluation of the measured value as an indirect benchmark for the change in the force effect, the direct force effect may also be determined and evaluated.

According to another embodiment of the disclosure, the measured value is formed by a measured value representing a penetration depth of the trocar and/or of the instrument in the body cavity. The penetration depth may provide indirect or direct evidence of a change in the force effect. An excessive penetration depth constitutes a risk to the patient. A calculation of the pivot point for the introduced trocar or the instrument may also be determined from the penetration depth in conjunction with the robotic arm of the trocar and/or the instrument. The penetration depth is advantageously determined in that at least one visual marker provided on the trocar and/or the instrument is detected and recorded by a visual measuring system, e.g., a camera system, and an evaluation of the recording of the visual marker with regard to the penetration depth is made. The monitoring system expediently has a trocar and/or an instrument with at least one visual marker for displaying the penetration depth of the trocar or instrument in the body cavity, and the measuring system is designed with at least one visual detection unit for detection and recording of the visual marker. The evaluation device is designed for determining the penetration depth from the recordings of the measuring system. The visual marker is advantageously formed by a visual length scale arranged on the trocar and/or the instrument, and the visual measuring system has at least one camera. A visual measuring system, in conjunction with visual markers, forms a simple, low-cost and yet accurate and flexible option for measuring the penetration depth of the trocar or the instrument without using additional detrimental radiation.

According to another embodiment, the measured value represents the pressure in the body cavity of the patient and may be implemented by using a pressure sensor or an insufflator. The shape of the surface of the body of the patient in the region above the body cavity, e.g. the abdominal wall, is decisively determined by introduced gas. The pressure may change significantly if a trocar slips or other movements enabling gas to escape are performed. Monitoring of the pressure is an important safety measure for detecting unforeseen displacements of the surface of the body or the position of the target region. The pressure may also be used to determine the pivot point of the trocar or instrument.

According to another embodiment of the disclosure, the measured value is formed by at least one torque value of at least one shaft of the robotic arm. The robotic arm may have at least two shafts that, in turn, have torque sensors for movement control. The forces acting on the pivot point of the trocar and/or instrument may be determined by one or more sensor(s) in the shafts of the robotic arm. The instrument may necessarily be permanently mounted on the robotic arm and introduced into the abdominal area of the patient through a trocar. Forces that act on the instrument act in the same way at the site of the robotic arm of the attached instrument. Furthermore, an initial pivot point (such as a patient entry point) is expediently defined by way of a suitable method. The torque sensors measure torque values that, by the comparison with reference values (initial pivot point), then register deviations of the forces exerted on the torque sensors. The forces may be caused by pushing or pulling the instrument mounted on the robotic arm due to a changed trocar position into a pivot point position other than the originally defined position. Deviations in all degrees of freedom may consequently be determined by installed torque sensors.

Multiple torque values are advantageously determined and used to determine the change in the force effect on the surface of the body and a compensating movement of the robotic arm to minimize the force effect. New pivot point positions may be calculated by an evaluation of the forces exerted on the torque sensors, e.g. with regard to their spatial orientation. Optimum and inverse movement directions of the robotic arm may also be calculated with regard to the forces exerted on the torque sensors in order to minimize the forces acting on the trocar and thereby the incision in the surface of the body. The pivot point may again be optimized by a compensating movement insofar as optimally minimal translatory forces act on the abdominal wall of the patient during rotational movements of the instrument around the pivot point.

The output device is advantageously formed by a monitor or touchpad or a loudspeaker. Further visual, acoustic, or haptic output media may also be used. An endoscopic robotic system with at least one robotic arm holding a trocar and/or an instrument guided through the trocar, having a monitoring system, is provided.

DETAILED DESCRIPTION

Figure 1:
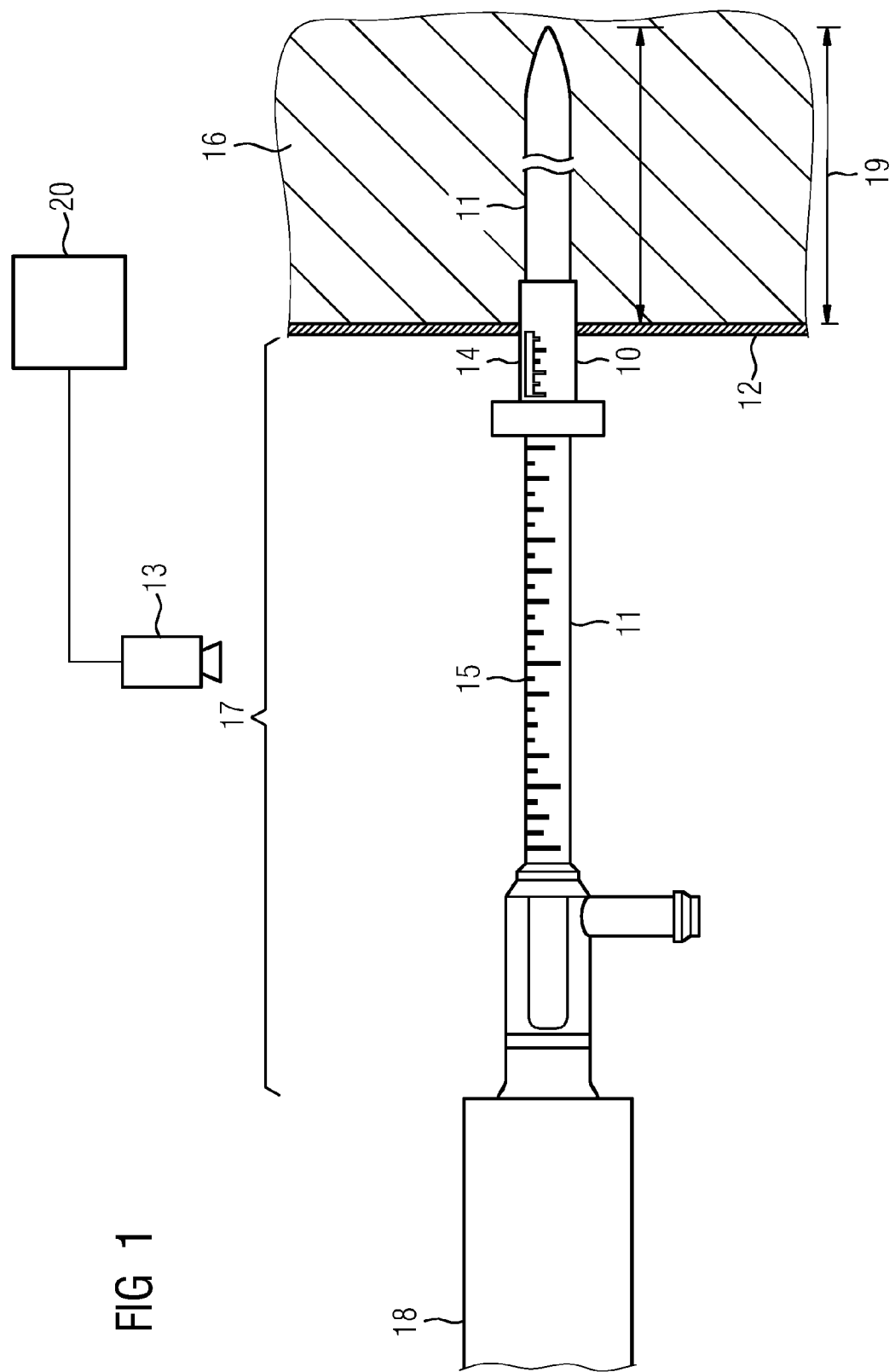
FIG. 1 illustrates a view of one embodiment of a monitoring system, a trocar and an instrument for a surgical procedure.

FIG. 1 illustrates a detail of a monitoring system with a visual measuring system for determining the penetration depth of an instrument 11 in an abdominal cavity 16 of a patient. A trocar 10 is introduced through an incision in the abdominal wall 12 of a patient and the instrument 11 is pushed through the trocar 10 into the abdominal cavity 16 of the patient. An instrument may be taken to mean a laparoscope or another tool that is fixed in length and introduced into the patient. The other end of the instrument 11 is held by a robotic arm 18 (partially depicted). Since the tip of the instrument 11 that is inside the abdominal cavity is not visible from the outside, a physician may have difficulty determining the penetration depth 19 of the instrument 11. The penetration depth 19 may be defined as the spacing of the distal end of the trocar 10 or instrument 11 from the surface of the body (abdominal wall 12) of the patient. Automation may be achieved via a length scale 15 arranged on the instrument 11 and a length scale 14 arranged on the trocar 10, both at least partially located outside of the abdominal cavity 17 and in the monitoring area 17 of a camera 13. By the camera 13, the penetration depth 19 of the instrument 11 in the body cavity may be determined by recording the length scale 15 thereof and may be evaluated via an evaluation system 20. In addition, a length scale 14 of the trocar 10 may be arranged on the trocar 10, also visible to the camera 13. The recording may also be evaluated by the evaluation system 20.

Figure 2:
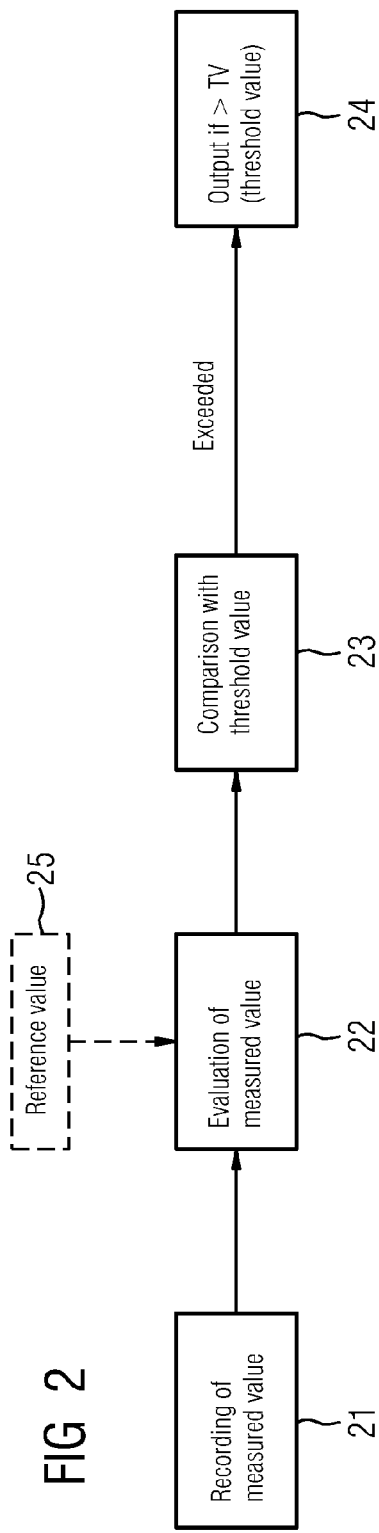
FIG. 2 illustrates a method for monitoring a surgical procedure, according to one embodiment.

A method may be implemented via the monitoring system illustrated in FIG. 1. Other measuring systems may also be used, however. FIG. 2 depicts a possible sequence of the method for automatically monitoring the penetration behavior of a trocar held by a robotic arm held and/or an instrument guided through the trocar into a body cavity through an incision in the surface of the body of a patient during a surgical procedure. The monitoring method may be carried out continuously or at regular intervals after the beginning of the surgical procedure. An expedient benefit is provided by recording one or more corresponding reference value(s) 25 at the beginning of the surgical method to be able to reliably deduce changes. In act 21, at least one measured value is recorded. The recorded value may allow the determination of a change in a force effect on the surface of the body or the incision in the surface of the body of the patient. Multiple measured values may also be recorded. Examples of such measured values include the penetration depth of the instrument or trocar, the pressure in the body cavity of the patient, or the torque value that may be determined on at least one shaft of the robotic arm. Measured values may also be used directly or indirectly for determining the pivot point of the instrument/trocar.

After determining the measured value, automatic evaluation is performed in act 22 with regard to the previously recorded reference value, in particular by the evaluation system or a system controller. A change in measured value for example may easily be determined, although a change in the force effect on the surface of the body or the incision in the surface of the body may also be determined. In act 23, the change in measured value or the change in the force effect is then compared with a threshold value. The threshold value may be fixed in advance by a user or be empirically chosen by the system. In act 24, an indication is automatically output if the threshold value has been detected as having been exceeded. An indication may be formed by an output on a monitor or another display unit (e.g. touchpad, etc.). An alarm sound or a visual alarm signal (e.g. flashing, color indication) or a haptic signal (e.g. vibration of a lever) may also be output.

Reference will be made below to the specific designs of the method in relation to the recorded measured values and further examples will be described in detail. Multiple examples may also be used simultaneously.

Use of the penetration depth as a measured value may be made by ascertaining the penetration depth of the instrument and the trocar in the abdominal cavity. The robotic arm may ascertain where the pivot point of the system for the trocar or the instrument is located in the abdominal wall. The penetration depth may be measured by the measuring system based on visual markers (e.g. length scales as depicted in FIG. 1), wherein a camera in sight of the instrument reads the measured values continuously or at intervals. The measuring system may automatically ascertain the length of the instrument and the penetration depth on the basis of the markings. The measuring system is sufficiently accurate to calculate the pivot point. If the measuring system is no longer able to ascertain values because the markings on the instrument are covered, visual, acoustic or mechanical warnings may likewise be output to the operator without interrupting the work using the system. The marking of the instrument is designed such that the whole instrument need not be visible. The instrument may be safely moved by the robotic arm in all remaining degrees of freedom for the patient by the automatic ascertainment, continual updating, and constant monitoring of the penetration depth of the instrument. The forces robotically applied by the surgeon to the instrument are correctly implemented and may not lead to incorrect movement e.g. movements injuring to the patient. The automatic detection of the instrument allows a change of instrument without calibration steps or value inputs having to be performed, increasing the flexibility of the system while simultaneously simplifying operation.

The pressure in the body cavity may be used as a measured value where monitoring the pressure in the abdominal cavity constitutes a significant safety measure for being able to react to unforeseen deformations of the abdomen, and therewith to changes in the pivot point. The shape of the abdominal wall is decisively determined by the introduced gas. The pressure may change significantly if a trocar slips or other movements enabling gas to escape are performed.

Figure 3:
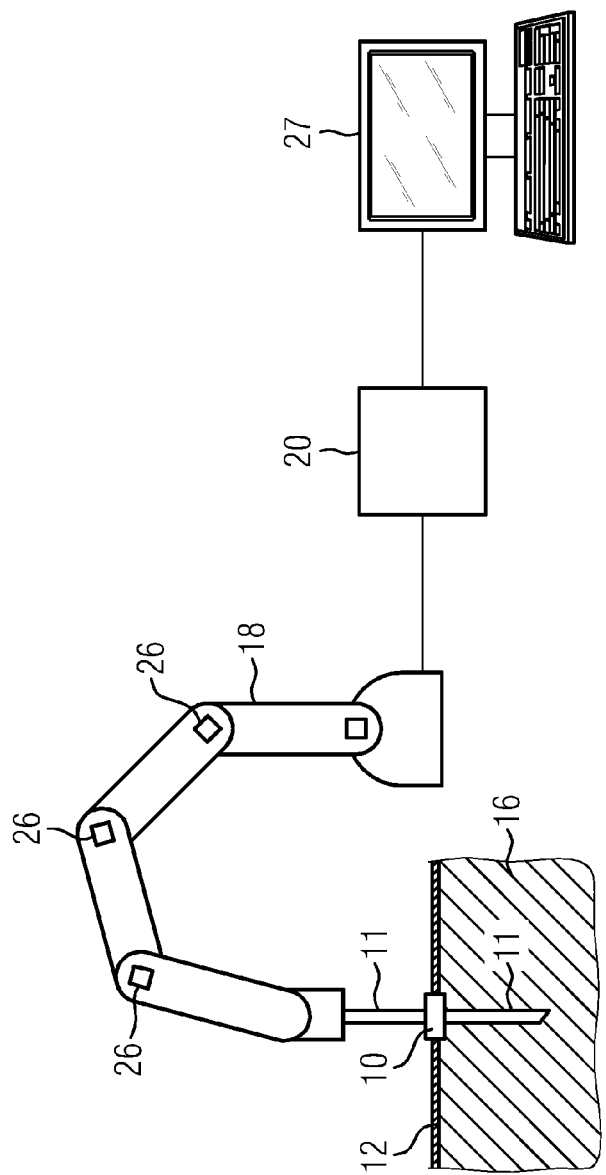
FIG. 3 illustrates an embodiment of an endoscopic robotic system having a robotic arm and a monitoring system.

FIG. 3 illustrates a monitoring system using torques of the robotic arm as measured values including a robotic arm 18 with multiple shafts and multiple torque sensors 26 arranged in the shafts. The evaluation system 20 is connected to the robotic arm 18, and a monitor 27 for displaying notes is also provided.

Monitoring of the applied and effective forces is made possible hereby in the case of all movements running orthogonally to the pivot point. Monitoring the forces is an advantageous safety measure for avoiding movements of the instruments that are dangerous to the patient. Existing robotic arm torque sensors may be used for monitoring. If the instrument is permanently mounted on the robotic arm and introduced through the trocar into the abdominal area of the patient, forces acting on the instrument act in the same way at the site of the robotic arm of the instrument. An advantage is provided if an initial pivot point (patient entry point) is defined at the beginning of the method. Events that may potentially change the pivot point translationally are changes in air pressure in the patient, deformations of internal organs, or deformations due to external effects. The torque sensor(s) may be arranged on all or some shafts of the kinematic chain of the robotic arm and may register deviations in the forces exerted on the torque sensors. The forces may be caused by pushing or pulling the instrument (e.g. endoscope/laparoscope) mounted on the robot due to a changed trocar position or a changed pivot point position other than the originally defined position. A plurality of installed torque sensors may determine deviations in all degrees of freedom. If the automatic method finds that changes have occurred, countermeasures may be taken to the advantage of the patient. The forces exerted on the torque sensors are evaluated with regard to spatial orientation. As a result, a new pivot point position or a movement direction of the robotic arm that is optimum and inverse with regard to the forces exerted on the torque sensors may be calculated to minimize or compensate the forces. The pivot point may therefore again be optimized to minimize translatory forces acting on the abdominal wall of the patient during rotational movements of the instrument around the pivot point.

Monitoring the forces applied during movement of the robotic arm, specifically in the pivot point of the instrument in the abdominal wall, is advantageous since injuries to the patient may otherwise occur. Forces may either be produced by the robotic arm or are exerted by the surgeon on the robotic arm as a movement control. If the robotic arm discovers a situation, corresponding signaling may occur and advantages are provided by limiting the force.

The embodiments relate to a method for automatically monitoring the penetration behavior of a trocar held by a robotic arm and/or an instrument guided through the trocar into a body cavity through an incision in the surface of the body of a patient during a surgical procedure, having the following acts: recording at least one measured value by which a change in a force effect on the surface of the body of the patient may be determined; automatic evaluation of the measured value with regard to a reference measured value; comparison of the change in the measured value or the change in the force effect with a threshold value; and outputting an indication in the event of the threshold value being exceeded.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

We claim:

1. A method for automatically monitoring the penetration behavior of a trocar held by a robotic arm, an instrument guided through the trocar, or the trocar and the instrument into a body cavity through an incision in the surface of the body of a patient during a surgical procedure, the method comprising:
    recording at least one measured value, a change in a force effect on the surface of the body of the patient determinable from the at least one measured value;
    automatically evaluating the at least one measured value based on a reference measured value;
    comparing a change in the measured value or the change in the force effect with a threshold value; and
    outputting an indication in event of the threshold value being exceeded.

2. The method of claim 1, wherein the measured value is evaluated with regard to the change in the force effect.

3. The method of claim 2, wherein the measured value is formed by a measured value representing a penetration depth of the trocar, of the instrument, or of the trocar and of the instrument in the body cavity.

4. The method of claim 2, wherein the measured value is formed by a pressure value representing the pressure in the body cavity of the patient.

5. The method of claim 2, wherein the measured value is formed by at least one torque value of at least one shaft of the robotic arm.

6. The method of claim 1, wherein the measured value is formed by a measured value representing a penetration depth of the trocar, of the instrument, or of the trocar and of the instrument in the body cavity.

7. The method of claim 6, further comprising:
    determining penetration depth by at least one visual marker provided on the trocar, on the instrument, or on the trocar and the instrument via a visual measuring system of a camera system;
    recording the visual marker via the camera system; and
    evaluating the recording of the visual marker with regard to the penetration depth.

8. The method of claim 1, wherein the measured value is formed by a pressure value representing the pressure in the body cavity of the patient.

9. The method of claim 1, wherein the measured value is formed by at least one torque value of at least one shaft of the robotic arm.

10. The method as claimed in claim 9, further comprising:
    determining the at least one torque value; and
    determining the change in the force effect on the surface of the body based on the at least one torque value; and
    determining a compensating movement of the robotic arm to minimize the force effect.

11. A monitoring system for automatically monitoring the penetration behavior of a trocar held on a robotic arm, an instrument guided through the trocar into a body cavity through an incision in the surface of the body of a patient, or the trocar and the instrument during a surgical procedure, the monitoring system comprising:
    at least one measuring system, the measuring system configured to
        record a measured value, a change in a force effect on the surface of the body of the patient determinable from the measured value;
    an evaluation device for evaluating the measured value; and
    an output device for outputting an indication.

12. A monitoring system of claim 11, further comprising:
    a trocar, an instrument, or a trocar and an instrument with at least one visual marker operable to:
        display a penetration depth of the trocar or instrument in the body cavity, wherein the measuring system further comprises at least one visual detector configured to
        detect a visual marker, and
        record the visual marker,
    wherein the evaluation device is configured to
        determine the penetration depth from the recorded, measured value of the measuring system.

13. The monitoring system of claim 12, wherein the visual marker is formed by a visual length scale arranged on the trocar, on the instrument, or on the trocar and on the instrument, and the visual measuring system has at least one camera.

14. The monitoring system of claim 13, wherein the output device further comprises:
    a monitor or a touchpad or a loudspeaker.

15. The monitoring system of claim 12, wherein the output device further comprises:
    a monitor or a touchpad or a loudspeaker.

16. The monitoring system of claim 11, wherein the measuring system is further configured to
    determine a measured value representing a pressure in the body cavity.

17. The monitoring system of claim 16, wherein the output device further comprises:
    a monitor or a touchpad or a loudspeaker.

18. The monitoring system of claim 11, wherein the measuring system further comprises:
    at least one torque sensor arranged on the robotic arm.

19. The monitoring system of claim 11, wherein the output device further comprises:
    a monitor or a touchpad or a loudspeaker.

20. An endoscopic robotic system comprising:
    at least one robotic arm holding a trocar, an instrument, or a trocar and an instrument guided through the trocar; and
    a monitoring system comprising:
        at least one measuring system, the measuring system configured to
            record a measured value, a change in a force effect on the surface of the body of the patient determinable from the measured value,
        an evaluation device for evaluating the measured value, and
        an output device for outputting an indication.

* * * * *